United States Patent [19]

Lin et al.

[11] Patent Number: 5,025,100

[45] Date of Patent: Jun. 18, 1991

[54] LIQUID AMINE TERMINATED DERIVATIVES OF DIGLYCIDYL ETHERS

[75] Inventors: Jiang-Jen Lin, Houston; George P. Speranza, Austin, both of Tex.

[73] Assignee: Texaco Chemical Company, White Plains, N.Y.

[21] Appl. No.: 475,516

[22] Filed: Feb. 6, 1990

[51] Int. Cl.$^5$ ............................................. C07D 303/23
[52] U.S. Cl. ..................................................... 549/551
[58] Field of Search ................ 549/551; 523/427, 421; 528/418

[56] References Cited

U.S. PATENT DOCUMENTS

| | | | |
|---|---|---|---|
| 3,538,184 | 11/1970 | Heer | 528/104 |
| 3,629,181 | 12/1971 | Heer et al. | 528/104 |
| 3,966,175 | 12/1976 | Schreiber et al. | 523/427 |
| 4,133,803 | 1/1979 | Klein | 525/423 |
| 4,348,505 | 9/1982 | DiBenedetto et al. | 549/401 |
| 4,485,229 | 11/1984 | Waddill et al. | 525/504 |
| 4,540,756 | 9/1985 | Hom | 528/99 |
| 4,578,412 | 3/1986 | Sellstrom et al. | 524/243 |
| 4,605,765 | 8/1986 | Miyomoto et al. | 564/367 |
| 4,608,404 | 8/1986 | Gardner et al. | 525/113 |
| 4,623,746 | 11/1986 | Kohli | 548/520 |
| 4,636,535 | 1/1987 | Wang et al. | 525/417 |
| 4,680,341 | 7/1987 | Newman-Evans | 529/98 |

*Primary Examiner*—Allen J. Robinson
*Assistant Examiner*—Mark W. Russell
*Attorney, Agent, or Firm*—Jack H. Park; Kenneth R. Priem; Carl G. Ries

[57] ABSTRACT

Tetrafunctional amine derivatives of digyclidyl ethers of Bisphenol A that are liquid at ambient temperatures and that are useful as curing agents for epoxy resins are disclosed together with the method by which they are prepared which comprises the steps of:

dissolving the diglycidyl ether in a solvent (acetone or methyl ethyl ketone) and adding a polyoxyalkylene diamine in the mole ratio of about 4 to about 5 moles of the diglycidyl ether per mole of said polyoxyalkylene diamine to provide an initial reaction mixture, heating the initial reaction mixture with agitation at a temperature of about 80° to about 160° C. for about 1 to about 4 hours sufficient to permit the diglycidyl ether to quantitatively react with the polyoxyalkylene diamine and to substantially completely volatilize the solvent to thereby form an intermediate reaction product, adding to the intermediate reaction product about 4 moles or more of a polyoxyethylene diamine per mol of initially used polyoxyalkylene diamine and heating the thus-formed second reaction mixture at a temperature of about 100° to about 150° C. for about 0.5 to about 5 hours, to form the tetrafunctional amine derivative.

4 Claims, No Drawings

LIQUID AMINE TERMINATED DERIVATIVES OF DIGLYCIDYL ETHERS

BACKGROUND OF THE INVENTION

1. Technical Field of the Invention

This invention relates to liquid amine terminated derivatives of diglycidyl ethers. More particularly, this invention relates to liquid amine terminated derivatives of diglycidyl ethers prepared from diglycidyl ethers of Bisphenol A and polyoxyalkylene diamines, as hereinafter defined. Still more particularly, this invention relates to liquid amine terminated derivatives of diglycidyl ethers prepared by reacting polyoxyethylene diamines with the epoxy terminated derivatives of glycidyl ethers of Bisphenol A and polyoxyalkylene diamines.

In another aspect, this invention relates to a method for preparing epoxy terminated derivatives of diglycidyl ethers. In yet another aspect, the present invention relates to a method of preparing amine terminated derivatives of diglycidyl ethers by reacting polyoxyethylene diamines with epoxy terminated amine derivatives of diglycidyl ethers of Bisphenol A and polyoxyalkylene diamines.

Both the epoxy terminated derivatives of the present invention and the amine terminated derivatives of the present invention are useful in the preparation of epoxy resins.

The epoxy terminated derivatives of diglycidyl

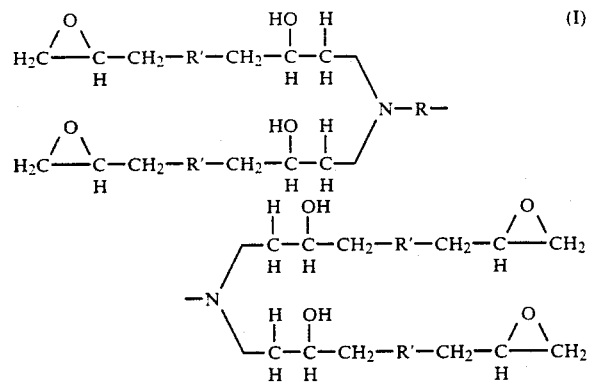

ethers of Bisphenol A may be characterized as follows:

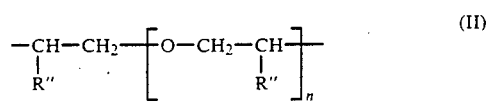

wherein:

R represents a polyoxyalkylene group having the formula:

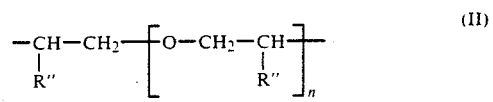

R" represents hydrogen, methyl or ethyl, n is a positive number having a value of about 2 to about 35, R' represents a glycidyl ether having the formula:

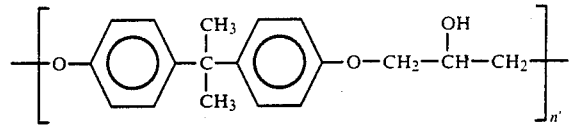
(III)

wherein n' represents 0 or a positive number having a value of 1 or 2.

The amine terminated derivatives of diglycidyl ethers of Bisphenol of the present invention may be characterized as amine terminated derivatives having the formula:

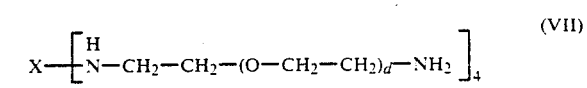
(VII)

wherein d is a positive number having an average value of 1 to about 4, and wherein X represents a group having the formula:

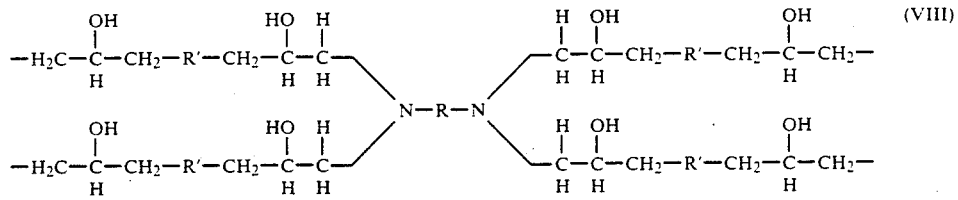
(VIII)

wherein:

R represents a polyoxyalkylene group having the formula:

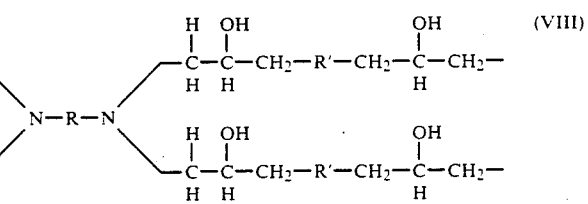
(II)

R" represents hydrogen, methyl or ethyl, n is a positive number having a value of about 2 to about 35, R' represents a glycidyl ether having the formula:

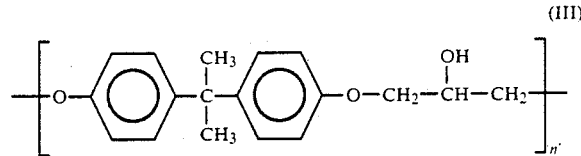
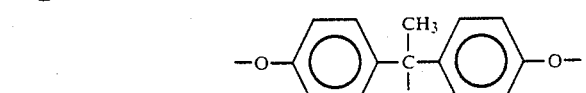
(III)

wherein n' represents 0 or a positive number having a value of 1 or 2.

Both the epoxy terminated derivatives and the amine terminated derivatives of the present invention, although with comparatively high molecular weights in the order of from about 2000 to about 10,000, are liquids at ambient temperatures. This is surprising, because the normally expected products from such reactants would be gels. Polyether amines are standard reagents for the curing of epoxy resins to solid products.

It has been discovered in accordance with the present invention that liquid epoxy terminated derivatives and liquid amine terminated derivatives having the formulas set forth above can be prepared by following the method of the present invention.

In accordance with the method of the present invention wherein epoxy terminated derivatives are to be prepared, a diglycidyl ether is dissolved in acetone and/or methylethyl ketone to prepare a charge solution which is mixed with from about 4 to 5 moles of a polyoxyalkylene diamine per mole of the diglycidyl ether to provide an initial reaction mixture and the initial reaction mixture is heated at a temperature of about 80° to about 160° C. for about 1 to 4 hours sufficient to permit the diglycidyl ether to quantitatively react with the polyoxyalkylene diamine and substantially completely volatilize the solvent to thereby form an epoxy terminated derivative of the diglycidyl ether.

In accordance with another embodiment of the present invention, the thus-formed reaction mixture containing the epoxy terminated derivatives of the diglycidyl ether is mixed with about 4 moles or more (e.g., 4 to 10 moles) of a polyoxyethylene diamine per mole of polyoxyalkylene diamine used in preparing the initial epoxy terminated reaction product.

2. Prior Art

It is well known that various polyamine compounds are widely used as raw materials for hardening agents of epoxy resins. For these resins, typical examples of useful polyamine compounds are aliphatic amines such as ethylenediamine, diethylenetriamine, triethylenetetramine, tetraethylenepentamine, pentaethylenehexamine, hexamethylenediamine, etc.; aromatic amines such as phenylenediamine, diaminophenylmethane, diaminophenylsulfone, etc.; aliphatic amines having aromatic ring, such as xylylenediamine, etc.; and alicyclic amines such as bisaminomethylcyclohexane, isophoronediamine, etc. These polyamine compounds each has a reactivity of the amino group as the specific feature caused by the active hydrogen and they are used for various purposes. Further, polyamine compounds which have been modified in a manner suitable for the specific polyamine compound have found a variety of uses and the modified compounds are used as hardening agents for epoxy resins.

Adducts from amines and diepoxides have long been used in industry as curing agents for epoxy resins.

It is known from U.S. Pat. No. 3,538,184 (November 1970) that a polyglycidyl ether can be reacted with a hexamethylenediamine to form solvent free liquid adducts of polyepoxides and polyamines which are suitable for use as curing agents for epoxy resins.

In U.S. Pat. No. 3,629,181 there is described a curing agent which comprises the adduct from a polyglycidyl ether of a polyphenyl and a cycloaliphatic or cycloaliphaticaliphatic di-primary diamine, in which at least one of the primary amino groups is bonded to an endocyclic carbon atom of a cycloaliphatic ring.

In U.S. Pat. No. 3,996,175 there are described moulding materials from epoxide resins based on Bisphenol A or on other bis- or polyphenols and epichlorohydrin which contain aromatic amines as curing agents.

U.S. Pat. No. 4,348,505 discloses the preparation of amine adduct curing agents utilizing epoxides of a functionality greater than two which dramatically enhance the chemical resistance properties of the cured epoxy products over results obtained from either free amines or the conventional amine adducts.

In U.S. Pat. No. 4,540,750 it was disclosed that the preparation of diethyl toluene diamine adduct curing agents with epoxides of a functionality of at least two enhances the performance characteristics of cured epoxy and urethane products U.S. Pat. No. 4,578,412 is directed to modified (i.e., extended) amine curing agents which are prepared by dissolving a solid elastomeric polyurethane such as RIM polyurethane in an amine of the type used for curing epoxy resins.

A novel polyamine compound made by reacting m-xylene diamine and epichlorohydrin in the presence of an alkali which is useful as a hardening agent for epoxy resins is disclosed in U.S. Pat. No. 4,605,765.

There are described in U.S. Pat. No. 4,608,404 compositions which contain specific groups of oligomeric diamine hardeners and epoxy compounds which when combined with structural fibers produce composites which have improved tensile properties, high compressive strengths and improved impact resistance and, in addition, demonstrate low moisture absorption.

In an article titled "High Solids Epoxy/Polyamide Coatings", V. Brytus discusses a new polyamide hardener which overcomes the compatibility problem brought about by reducing the molecular weight of epoxy/polyamidoamine maintenance coatings in an attempt to lower the volatile organic content. See *Journal of Coatings Technology*, Vol. 58, No. 740, September 1986. The polyamide has controlled levels of imidazoline and other constituents having an affinity for the Bisphenol A moiety. A two-step method of producing N,N'-dimethyl diamine epoxide compounds for use as epoxide polyaddition compounds is described in U.S. Pat. No. 4,623,746. The resins formed using this compound as a curative can be produced with improved strength, toughness and hot/wet properties.

Wang et al. disclose in U.S. Pat. No. 4,636,535 curable compositions comprising epoxide prepolymers and polyamidobenzoates, alone or combined with reinforcements such as graphite fibers.

In U.S. Pat. No. 4,680,341 epoxy resin systems are disclosed which exhibit good tensile properties and good moisture sensitivity which are made by copolymerizing tetraglycidates with a polyamine curing agent.

From the preceding discussion it is apparent that compositions with a variety of properties which are the product of a wide range of amine and epoxide components are useful in the field of epoxy curing resins.

SUMMARY OF THE INVENTION

In accordance with the present invention, products that are useful in the preparation of epoxy resins are provided, such products constituting epoxy terminated derivatives of polyoxyalkylene diamines and diglycidyl ethers of Bisphenol A, as hereinafter defined. The present invention is also directed to amine derivatives of the epoxy terminated derivatives of diglycidyl ethers of Bisphenol A prepared by reacting polyoxyethylene diamines, as hereinafter specified, with the epoxy terminated derivatives in the manner hereinafter described.

An advantage of both the epoxy terminated and the amine terminated derivatives of diglycidyl ethers of bisphenol is that the products are liquid at ambient temperatures and can be used as epoxy curing agents in preparing epoxy resins wherein added flexibility is an important property.

It has been discovered in accordance with the present invention that the solvent that should be used is either acetone or methylethyl ketone (MEK).

The starting materials of the present invention are diglycidyl ethers of Bisphenol A, polyoxyalkylene diamines, polyoxyethylene diamines and a solvent.

If the symbol "E" represents a diglycidyl ether of Bisphenol A, the symbol "A" represents the polyoxyalkylene diamine and the symbol "A+" represents the polyoxyethylenediamine, then the reactions and reaction products of the present invention can be visualized thusly:

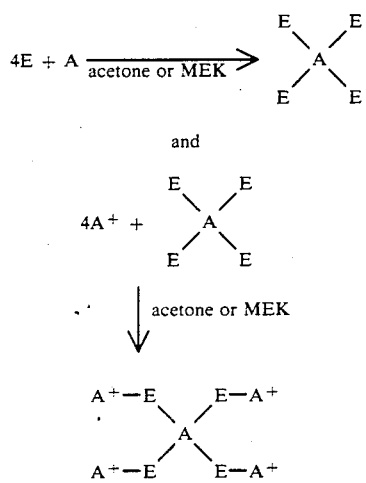

As can be more easily seen from the foregoing, the process and products of the present invention provide an improvement in the act of preparing epoxy resins wherein a significant portion of the Bisphenol A component is "prereacted" prior to the final epoxy resin formation step to liquid intermediates that are easy to prepare, easy to store and easy to use.

Key factors that are involved include the discovery that it is necessary to use either acetone or methyl ether ketone as a solvent in the process of the present invention and the discovery of the need to use a polyoxyethylene diamine in the second step of the process.

The Diglycidyl Ethers of Bisphenol A

The diglycidyl ethers of Bisphenol A to be used in accordance with the present invention are diglycidyl ethers having the formula:

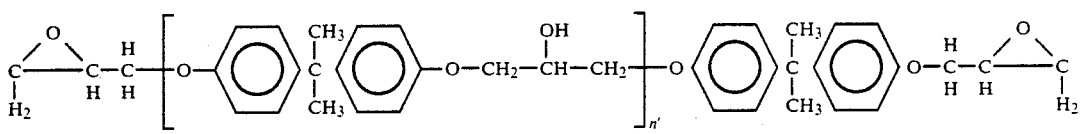

wherein n' represents 0 or a positive number having a value of 1 to about 2.

The Polyoxyalkylene Diamine Starting Material

The polyoxyalkylene diamines to be used as starting materials in accordance with the present invention are polyoxyalkylene diamines having the formula:

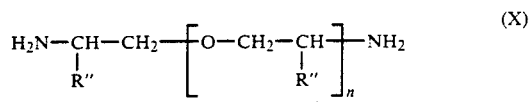

wherein n is a positive number having a value of about 2 to about 35 and wherein R" represents hydrogen, methyl or ethyl.

Representative products having this structural formula include polyoxypropylene diamines (wherein R" is methyl) having an average molecular weight of about 230 wherein the value of n is between 2 and 3 (Jeffamine ® D-230 amine), polyoxypropylene diamines having an average molecular weight of about 400 wherein n has a value between about 5 and 6 (Jeffamine ® D-400 amine), and a polyoxypropylene diamine product having an average molecular weight of about 2,000 wherein n has a value of about 33 (Jeffamine ® D-2000 amine).

Another appropriate class of polyoxyalkylene diamines, containing both ethylene oxide and propylene oxide, which may be used are polyoxypropylene diamines that are sold by the Texaco Chemical Company as Jeffamine ® ED-series products having the formula:

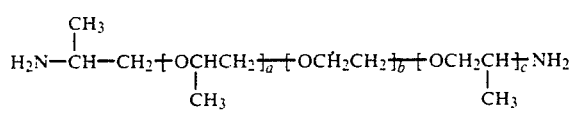

wherein a+c equals a number having a value of from about 2 to about 10 and b is a number having a value of from about 1 to about 50.

Examples of products having this general formula include a commercial product having an average molecular weight of about 600 where the value of b is about 8.5 and the value of a+c is about 2.5 (Jeffamine ® ED-600), a commercial product having an average molecular weight of about 900 wherein the value of a+c is again about 2.5, but the value of b is about 15.5 (Jeffamine ® ED-900). Other examples are those wherein a+c has a value of about 2.5 including a product having an average molecular weight of about 2,000 wherein the value of b is about 40 (Jeffamine ® ED-2001).

The Polyoxyethylene Diamine Starting Material

The polyoxyethylene diamine starting material to be used in accordance with the present invention are poly-

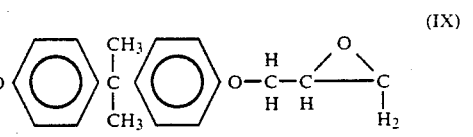

oxyethylene diamines having the formula:

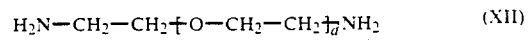

wherein d is a positive number having a value of 1 to about 4.

Representative examples of polyoxyethylene diamines include:

Jeffamine ® EDR-148 is an amine terminated triethylene glycol having the formula:

H₂N—CH₂CH₂—O—CH₂CH₂—O—CH₂CH₂—NH₂

Jeffamine ® EDR-192 is an amine terminated tetraethylene glycol having the formula:

H₂N—CH₂CH₂—O—CH₂CH₂—O—CH₂CH₂—O—CH₂CH₂—NH₂

Preparation of the Epoxy Terminated Derivatives of Polyoxyalkylene Diamines and Diglycidyl Ethers of Bisphenol A In accordance with the present invention, epoxy terminated derivatives of diglycidyl ethers of Bisphenol A and polyoxyalkylene diamines are prepared by the following sequence:

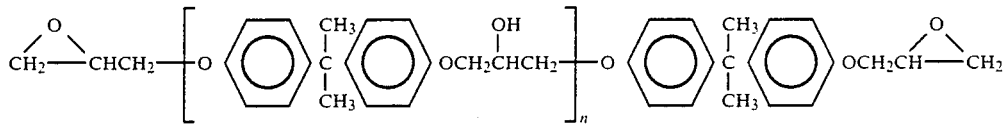

A diglycidyl ether of Bisphenol A having formula IX given above is dissolved in either acetone or methylethyl ketone. Acetone is the preferred solvent and gives the best results.

The thus prepared solution is added to a reaction vessel and a polyoxyalkylene diamine having the composition as set forth in formula X above is added, the amount of polyoxyalkylene diamine added being such that there is provided about 4 to 5 moles of the diglycidyl ether per mole of polyoxyalkylene diamine. The preferred ratio is a ratio of about 4.5 moles of the diglycidyl ether per mole of polyoxyalkylene diamine.

The thus formed reaction mixture is heated with agitation at a temperature within the range of about 80° to about 160° C. for about 1 to about 4 hours sufficient to permit the diglycidyl ether to quantitatively react with the polyoxyalkylene diamine and to substantially completely volatilize the ketone solvent initially charged to the reaction vessel. Thereafter, if desired, the epoxy terminated derivative can be recovered from the reaction mixture and will have a formula as given in formula I above.

Preparation of the Amine Derivatives of Diglycidyl Ethers of Bisphenol A

In accordance with another embodiment of the present invention, an epoxy terminated derivative of Bisphenol A as prepared in the manner just described, is further reacted with a polyoxyethylene diamine having the formula XII, given above.

This can be accomplished by further adding to the reaction mixture described above about 4 moles or more, such as 4 to 10 moles of the polyoxyalkylene per mole of said polyoxyalkylene diamine starting material used in the preparation of the epoxy terminated diglycidyl ether. In this situation, the epoxy terminated diglycidyl derivative is, in effect, an intermediate reaction product and when mixed with the polyoxyethylene diamine provides a second reaction mixture.

The second reaction mixture is heated at a temperature of about 100° to about 150° C. for about 0.5 to about 5 hours and thereafter a tetrafunctional amine derivative having the formula VII given above is recovered.

It is known to use amines such as aliphatic or aromatic amines for curing 1,2-epoxy resins as shown, for example, by Waddill U.S. Pat. Nos. 4,139,524 and Marquis et al. 4,162,358. See also, the textbook "Handbook of Epoxy Resins" by H. Lee and K. Neville, McGraw-Hill Book Company, 1967.

Generally the vicinal epoxide compositions that can be cured using the curing agents of this invention are organic materials having an average of more than one reactive 1,2-epoxide group. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, halogenated phenyl groups and the like.

The most widely used epoxy resins are diglycidyl ethers of bisphenol A:

where n equals an integer of 1 or 2.

However, these epoxides are representative of the broader class of epoxide compounds that are useful in making epoxy resins.

A widely used class of polyepoxides that can be cured according to the practice of the present invention includes the resinous epoxy polyethers obtained by reacting an epihalohydrin, such as epichlorohydrin, and the like, with either a polyhydric phenol or a polyhydric alcohol. An illustrative, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'-dihydroxydiphenylmethylpropylmethane, 2,3'-dihydroxydiphenylethylphenylmethane, 4,4'-dihydroxydiphenylmethane, 4,4'-dihydroxydiphenylbutylphenylmethane, 2,2'-dihydroxydiphenylditolylmethane, 4,4'-dihydroxydiphenyltolylmethyl-methane and the like. Other polyhydric phenols which may also be co-reacted with an epihalohydrin to provide these epoxy polyethers are such compounds as resorcinol, hydroquinone, substituted hydroquinones, e.g., tert-butylhydroquinone, and the like.

Among the polyhydric alcohols that can be co-reacted with an epihalohydrin to provide the resinous epoxy polyethers are such compounds as ethylene glycol, propylene glycol, butylene glycols, pentane diols, bis(4-hydroxycyclohexyl)dimethylmethane, 1,4-dimethylolbenzene, glycerol, 1,2,6-hexanetriol, trimethylolpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, such as 2,2'-, 3,3'-tetrahydroxydipropylsulfide and the like, mercapto alcohols such as α-monothioglycerol, α,α'-dithioglycerol, and the like, polyhydric alcohol partial esters, such as monostearin, pentaerythritol monoacetate, and the like, and halogenated polyhydric alcohols such as the monochlorohydrins of glycerol, sorbitol, pentaerythritol and the like.

Another class of polymeric polyepoxides that can be cured by means of the above-described curing agents includes the epoxy novolac resins obtained by reacting, preferably, in the presence of a basic catalyst, e.g., sodium or potassium hydroxide, an epihalohydrin, such as epichlorohydrin, with the resinous condensate of an aldehyde, e.g., formaldehyde, and either a monohydric phenol, e.g., phenol itself, or a polyhydric phenol. Further details concerning the nature and preparation of these epoxy novolac resins can be obtained in Lee, H. and Neville, K. "Handbook of Epoxy Resins".

It will be appreciated by those skilled in the art that the polyepoxide compositions that can be cured according to the practice of the present invention are not limited to the above described polyepoxides, but that these polyepoxides are to be considered merely as being representative of the class of polyepoxides as a whole.

The amount of curing agent that is employed in curing polyepoxide compositions will depend on the amine equivalent weight of the curing agent employed. The total number of equivalents of amine group is preferably from about 0.8 to about 1.2 times the number of epoxide equivalents present in the curable epoxy resin composition with a stoichiometric amount being most preferred.

Various conventionally employed additives can be admixed with these polyepoxide-containing compositions prior to final cure. For example, in certain instances it may be desired to add minor amounts of other co-catalysts, or hardeners, along with the curing agent system herein described. Conventional pigments, dyes, fillers, flame retarding agents and other compatible natural and synthetic resins can also be added.

The invention will be further illustrated by the following specific examples which are given by way of illustration and not as limitations on the scope of this invention.

FIRST INVENTION: EPOXY TERMINATING JEFFAMINE AMINE

Example 1 (6285-64) Products from Jeffamine D-400 and Epon 828 (1:4.5 molar ratio)

To a 1 liter, three-necked flask equipped with a thermometer, Dean-Stark trap, stirrer and nitrogen line was charged Jeffamine D-400 (60 g, 0.15 M) and Epon 828 (253 g, 0.675 mole) in acetone (100 ml). The mixture was heated to 100° C. for 2 hours to remove acetone and to obtain a transparent, light-yellow semisolid.

Example 2 (6285-32) Products from Jeffamine D-400 and Epon 828 (1:3 molar ratio) (Comparative)

To a 500 ml three-necked flask equipped with a thermometer, Dean-Stark trap, stirrer and N2 line, was charged D-400 (20 g, 0.05 mole) and Epon 828 (56 g, 0.15 mole) in acetone (50 ml). The mixture was heated to the refluxing temperature. During the process of removing acetone, the mixture was turned into a gel product. The result shows that ratios below 4 of D-400 forms a gelled product.

Example 3 (6285-6) Products from Jeffamine D-400 and Epon 828 (1:2 molar ratio) (Comparative)

To a 250 ml three-necked flask equipped with a thermometer, Dean-Stark trap, mechanical stirrer and nitrogen inlet line, was charged Jeffamine D-400 (30 g, 0.075 mole) and Epon 828 (56 g, 0.15 mole) in acetone (50 ml). The mixture was heated to 67 to 75° C. for ca. 2 hours. While reaction temperature was raising to 90° C., gel formation was observed. Again, the experiment indicated the 1:2 molar ratio of D-400 to Epon 828 was not suitable for avoiding gel formation.

Example 4 (6300-3) Products from Epon 828 and Jeffamine ED-2001 with Acetone (4:1 molar ratio)

To a 250 ml three-necked flask equipped with a thermometer, stirrer, Dean-Stark trap and N2 line, was charged Epon 828 (75 g, 0.2 moles), ED-2001 (100 g, 0.05 moles) in acetone (50 ml). The mixture was heated to remove solvent to 140° C. for ca. 2 hours. The resulting material was an attractive, transparent, light-colored liquid.

Example 5 (6285-98) Products from Dimer Amine and Epon 828 in Acetone (1:6 molar ratio)

To a 250 ml three-necked flask equipped with a thermometer, Dean-Stark trap, stirrer and nitrogen inlet line was charged a 36 carbon atom dimer amine having a molecular weight of about 590 (29.6 g, 0.05 M) and Epon 828 (112 g, 0.3 M) in acetone (100 ml). The mixture was heated slowly to remove acetone. The mixture was then heated to 150° C. under vacuum for ca. 1 hour. The resulting product was a viscous brown liquid (139 g).

Example 6 (6285-73) Products from Epon 828 and Jeffamine ED-2001 (4:1 molar ratio) (Comparative)

To a 250 ml three-necked flask equipped with a thermometer, mechanical stirrer and N2 line was charged Epon 828 (Shell product, 75 g, 0.2 moles) and Jeffamine ED-2001 (100 g, 0.05 moles). There was no acetone used. The mixture was heated to 100°-115° C. for about 2 hours. Gel formation was observed. The presence of acetone is the important factor for preparing a non-gelled product.

Example 7 (6285-69) Products from Dimer Amine and Epon 828 Without using Acetone Solvent (Comparative)

To a 250 ml three-necked flask equipped with a thermometer, Dean-Stark trap, stirrer and N2 line was charged dimer amine (29.6 g, 0.05 M) and Epon 828 (112 g, 10.3 M). The mixture was heated to 100° C. for ca. 2 hours. The recovery product was rubbery, gel-like material. The experiment demonstrated the importance of acetone requisite.

Example 8 (6285-60) Products from Jeffamine D-2000 and Epon 828 (1:4.5 molar ratio)

To a 1 liter three-necked flask equipped with a thermometer, Dean-Stark trap, stirrer and nitrogen line, was charged D-2000 (200 g, 0.1 M) and Epon 828 (168 g, 0.45 M) and acetone (100 ml). The mixture was heated to reflux, the acetone was removed and then the product was heated at 120° C. for 2 hours. A transparent liquid product was obtained. The analyses indicated the amine content was 0.53 meq/g; total acetylatables 4.11 meq/g, and viscosity 14,000 cs/25° C.

Example 9 (6285-60-1) Usage of Product

The mixture of 6285-60, 20 g (adduct of D-2000:Epon ® 828 at 1:4.5 ratio) and EDR-148 (1.0 g) were mixed carefully and poured into a mold. The liquid mixture was cured overnight at 80° C. to afford a flexible new material with high integrity.

Example 10 (6285-46) Products from D-2000-Epon 828-EDR-148 (1:4:9 molar ratio)

To a 500 ml three-necked flask equipped with a thermometer, stirrer, Dean-Stark trap and $N_2$ line, was charged Jeffamine D-2000 (100 g, 0.05 M) and Epon 828 (74.8 g, 0.2 mole) in acetone (50 ml). The mixture was heated to 70°-88° C. to remove acetone for one hour. Then, Jeffamine EDR-148 (66.6 g, 0.45 mole) in acetone (30 ml) was added. The final mixture was heated slowly to 120°-130° C. and subjected to vacuum for ca. 1 hour. The resulting product (237 g) was yellowish-brown liquid having analyses of total amine 4.01 meq/g, hydroxyl number 5.32 meq/g and viscosity 5,500 cs/50° C.

Example 11 (6285-47) Products from D-400-Epon 828-EDR-148 (1:4.5:10 molar ratio)

To a 500 ml three-necked flask equipped with a thermometer, stirrer, Dean-Stark trap and $N_2$ line, was charged Jeffamine D-400 (20 g, 0.05 mole) in acetone (20 ml) and Epon 828 (84 g, 0.225 mole) in acetone (80 ml). The mixture was heated slowly to remove acetone over a two hour period of time. Then, Jeffamine EDR-148 (74 g, 0.5 mole) in acetone (70 ml) was added. The process of removing solvent was repeated. The mixture was heated to 130° C. under reduced pressure. The resulting product (185 g) was viscous, transparent brown liquid having analyses of 23,000 cs/50° C., total amine content 5.82 meq/g, hydroxyl number 7.48 meq/g.

Example 12 (6250-95) Products from D-400-Epon 828-EDR-148 (1:2:2 molar ratio) (Comparative)

To a 500 ml three-necked flask equipped with a thermometer, Dean-Stark trap, mechanical stirrer and nitrogen inlet line, was charged Jeffamine D-400 (60 g, 0.15 mole) in acetone (30 g) and Epon 828 (112 g, 0.30 moles) in acetone (100 g). The mixture was heated to 70°-80° C. for one hour. Then Jeffamine EDR-148 (44.4 g, 0.30 moles) in acetone (40 g) was added and continued heating at 70°-80° C. A gel material was obtained after acetone was removed. This experiment demonstrated the importance of molar ratio of D-400-Epon 828-EDR-148.

Example 13 (6285-28) Products from D-2000-Epon 828-EDR-192 (1:3:4 molar ratio)

To a 500 ml three-necked flask equipped with a thermometer, stirrer, Dean-Stark trap and $N_2$ inlet line, was charged Jeffamine D-2000 (160 g, 0.08 mole) in acetone (60 g) and Epon 828 (90 g, 0.24 mole) in acetone (90 g). The mixture was heated to reflux and then to 100° C. Acetone was removed during the process. Then, EDR-192 (74 g, 0.385 mole) in acetone (50 ml) and water (50 ml) was added. The process of removing solvents was repeated by heating the mixture to 130° C. for ca. 2 hours. The resulting product was viscous liquid, having the following analyses: viscosity: 22,000 cs/50° C., total amine 2.79 meq/g and hydroxyl number 5.18 meq/g. The molar ratio of amine to epoxide is the important factor for controlling the gelling characteristics of the product.

Example 14 (6285-55) Products from D-2000-Epon 828-EDR-192 (1:4.5:5.0 molar ratio)

To a 500 ml three-necked flask equipped with a thermometer, stirrer, Dean-Stark trap and $N_2$ line, was charged D-2000 (100 g, 0.05 mole) and Epon 828 (84 g, 0.225 mole) in acetone (80 ml). The mixture was heated to the refluxing temperature and acetone was removed. Then, EDR-192 (48 g, 0.25 mole) in acetone (50 ml) was added. During the process of removing acetone, gel formation was observed. This experiment defined the limitations of molar ratio of Jeffamine amine(I)-Epon 828-Jeffamine amine(II).

Example 15 (6285-24) Products from D-2000-Epon 828-EDR-192 (1:2:2 molar ratio) (Comparative)

To a resin flask equipped with a thermometer, Dean-Stark trap, stirrer and $N_2$ inlet line, was charged D-2000 (160 g, 0.08 mole) in acetone (60 g) and Epon 828 (60 g, 0.16 moles) in acetone (60 g). The mixture was heated to 70°-100° C. for four hours while removing acetone through a Dean-Stark trap. Then EDR-192 (31 g, 0.16 moles) in acetone (30 g) and water (15 g) was added. The mixture was heated slowly to about 100° C. and then 130° C. for four hours under aspirator vacuum. The recovered product was a rubbery brown solid.

Example 16 (6285-1) Products from D-2000-Epon 828-EDR-148 (1:2:2 molar ratio) (Comparative)

To a 500 ml three-necked flask equipped with a thermometer, Dean-Stark trap, mechanical stirrer and nitrogen inlet line, was charged Jeffamine D-2000 (160 g, 0.08 mole), Epon 828 (60 g, 0.16 mole) and acetone (60 g). The mixture was heated to 50°-60° C. for 2 hours. A sample of ca. 19 g was taken for analysis. Then Jeffamine EDR-148 (22 g, 0.149 mole) in acetone (20 g) was added. The reaction temperature was raied to remove acetone until dryness. The resulting material was milky-white solid. The total amine analysis showed 1.85 meq/g. After standing at room temperature, the product became two layers of liquid (brown, about 5 wt. %, top layer) and solid (soft, milky-white, about 95 wt. %, bottom layer), indicating the mixture was not homogeneous.

Example 17 (6285-60-2) Products from D-2000-Epon 828-EDR-148 (1:4.5:6.75 molar ratio)

To a 1 liter, three-necked flask equipped with a thermometer, stirrer, Dean-Stark trap and nitrogen line, was charged product from (6285-60-1) ca. 184 g and EDR-148 (50 g, 0.338 mole) in acetone (50 ml). The mixture was heated to remove acetone. During the process, gel formation took place.

Example 18 (6285-46) Usage of Product

The sample of 6285-46 (21.6 g) and Epon 828 (20 g) was mixed well and poured into a mole and cured at 60° C. for 2 hours to give a flexible, tough material.

It is noted that:

(1) In order to avoid gel product, the proper ratio of amine to epoxy resin is required. The first step requires at least a 1:4 molar ratio of amine to epoxide.

(2) The second step, reaction of tetrafunctional epoxy resin with active Jeffamine amine, a large excess of EDR-148 or EDR-192 was needed.

(3) Acetone or a low boiling ketone is essential for preparing these products.

Having thus described our invention, what is claimed is:

1. An epoxy terminated derivative of a diglycidyl ether having the formula:

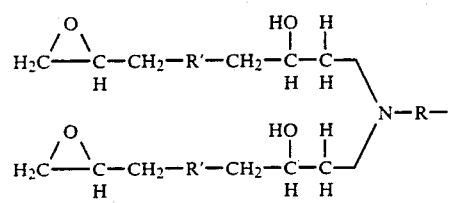
(I)

wherein:

R represents a polyoxyalkylene group having the formula:

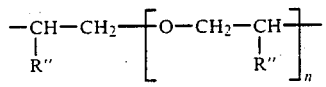
(II)

R" represents hydrogen, methyl or ethyl, n is a positive number having a value of about 2 to about 35, R' represents a glycidyl ether having the formula:

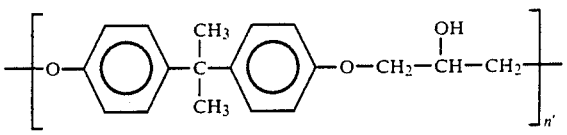
(III)

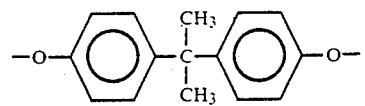

wherein n' represents 0 or a positive number having a value of 1 or 2.

2. An epoxy terminated derivative as in claim 1 wherein R represents an oxypropylene group having the formula:

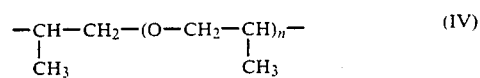
(IV)

wherein n is a positive number having an average value of about 2 to about 35.

3. An epoxy terminated derivative as in claim 1 wherein R represents an oxyalkylene group having the formula:

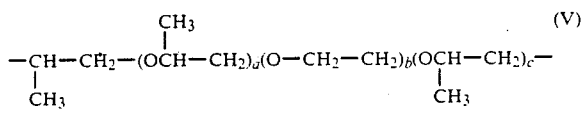
(V)

wherein a+c equals a positive number having a value of about 2 to about 10 and b is a positive number having an average value of from about 1 to about 50.

4. An epoxy terminated derivative as in claim 1 wherein R represents an oxypropylene group having the formula:

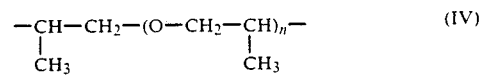
(IV)

wherein n is a positive number having an average value of about 33.

* * * * *